United States Patent [19]

Pascal et al.

[11] 4,259,334
[45] Mar. 31, 1981

[54] PIPERAZINES AND THERAPEUTIC UTILITY

[75] Inventors: Jean C. Pascal, Cachan; Henri Pinhas, Paris, both of France

[73] Assignee: Laroche Navarron S.A., Puteaux, France

[21] Appl. No.: 27,475

[22] Filed: Apr. 5, 1979

[30] Foreign Application Priority Data

Apr. 27, 1978 [GB] United Kingdom ............... 16744/78

[51] Int. Cl.³ .................. A61K 31/495; C07D 295/08
[52] U.S. Cl. .................................... 424/250; 544/391; 544/398; 544/402
[58] Field of Search ...................... 544/391, 398, 402; 424/250

[56] References Cited

U.S. PATENT DOCUMENTS

| | | | |
|---|---|---|---|
| 3,793,322 | 2/1974 | Shroff et al. | 544/391 |
| 3,951,986 | 4/1976 | Maruyama et al. | 260/293.73 |
| 4,115,569 | 9/1978 | Weber et al. | 424/250 |

Primary Examiner—Anton H. Sutto
Attorney, Agent, or Firm—Young & Thompson

[57] ABSTRACT

The invention relates to compounds having the formula:

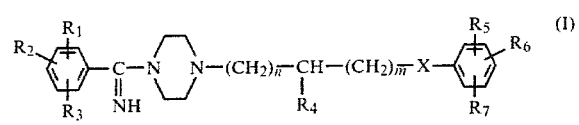

in which:

the substituents $R_1$, $R_2$ and $R_3$ represent independently from each other a hydrogen atom, a halogen atom, a trifluoromethyl radical, a saturated or unsaturated straight- or branched-chain $C_{1-6}$ alkyl radical, a $C_{1-6}$ alkoxy radical the alkyl moiety of which may be saturated or unsaturated and straight- or branched-chained, a benzyloxy radical or a hydroxy radical;

the substituents $R_5$, $R_6$ and $R_7$ represent independently from each other a hydrogen atom, a halogen atom, a trifluoromethyl radical, a straight- or branched-chain saturated or unsaturated $C_{1-6}$ alkyl radical, a $C_{1-6}$ alkoxy radical the alkyl moiety of which may be saturated or unsaturated and straight- or branched-chained, or a hydroxy radical;

the substituent $R_4$ represents a hydrogen atom, a $C_{1-6}$ alkyl radical or a hydroxy radical, m and n represent independently a number equal to 0, 1 or 2, X represents an oxygen atom, a sulfur atom or a single bond, and their pharmaceutically acceptable acid addition salts.

These compounds are therapeutically useful for the control of the cardiovascular system.

3 Claims, No Drawings

PIPERAZINES AND THERAPEUTIC UTILITY

This invention relates to new piperazine methanimine derivatives, to a process for their preparation and to their therapeutic applications.

This invention relates to compounds having the general formula:

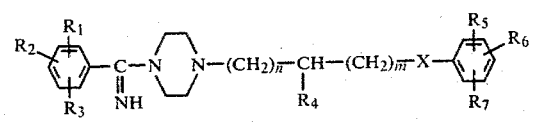

in which:

the substituents $R_1$, $R_2$ and $R_3$ represent independently from each other a hydrogen atom, a halogen atom, a trifluoromethyl radical, a saturated or unsaturated straight- or branched-chain $C_{1-6}$ alkyl radical, a $C_{1-6}$ alkoxy radical the alkyl moiety of which may be saturated or unsaturated and straight- or branched-chained, a benzyloxy radical or a hydroxy radical;

the substituents $R_5$, $R_6$ and $R_7$ represent independently from each other a hydrogen atom, a halogen atom, a trifluoromethyl radical, a straight- or branched-chain saturated or unsaturated $C_{1-6}$ alkyl radical, a $C_{1-6}$ alkoxy radical the alkyl moiety of which may be saturated or unsaturated and straight- or branched-chained, or a hydroxy radical;

the substituent $R_4$ represents a hydrogen atom, a $C_{1-6}$ alkyl radical or a hydroxy radical, m and n represent independently a number equal to 0, 1 or 2, X represents an oxygen atom, a sulfur atom or a single bond, and their pharmaceutically acceptable acid addition salts.

The addition salts may be those formed with hydrohalic, sulfuric, nitric, phosphoric, formic, acetic, maleic, fumaric, methane sulfonic, lactic, succinic, tartaric acids and acidic metal salts such as disodium orthophosphate and monopotassium sulfate. The free bases may exist in hydrated or substantially anhydrous form.

A particular class of the compounds of the formula (I) is that consisting of the compounds in which:

the substituents $R_1$, $R_2$ and $R_3$ represent independently a hydrogen atom, a trifluoromethyl radical, a saturated $C_{1-4}$ alkyl radical, a saturated $C_{1-4}$ alkoxy radical, a benzyloxy radical or a hydroxy radical, the substituents $R_5$, $R_6$ and $R_7$ represent independently a hydrogen atom, a halogen atom or a $C_{1-4}$ alkyl radical, the substituent $R_4$ represents a hydrogen atom or a methyl radical, m and n represent independently a number equal to 0, 1 or 2, X represents an oxygen atom, a sulfur atom, or a single bond, and their pharmaceutically acceptable acid addition salts.

The compounds of the formula (I) may be prepared by reacting a lower alkyl iminoate having the formula:

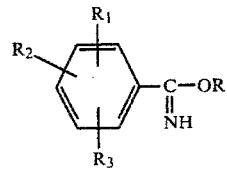

in which R is a lower alkyl radical, typically a $C_{1-2}$ alkyl radical, and $R_1$, $R_2$ and $R_3$ have the meanings given for formula (I), with a piperazine having the formula:

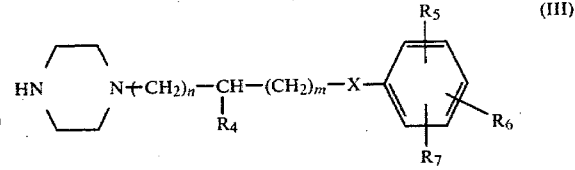

in which $R_4$, $R_5$, $R_6$, $R_7$, m and n have the meanings given for formula (I), in alcohol solution and in the hot.

The compounds of the formula (II) are obtained in conventional manner, by reacting a nitrile having the formula:

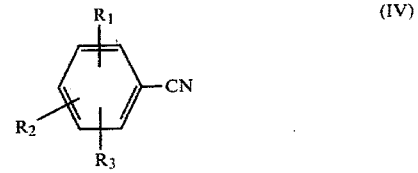

as a solution in ethyl oxide-alcohol (typically methanol or ethanol), in the presence of hydrochloric acid.

The compounds of the formula (III) may be obtained by reaction of a halogen derivative having the formula:

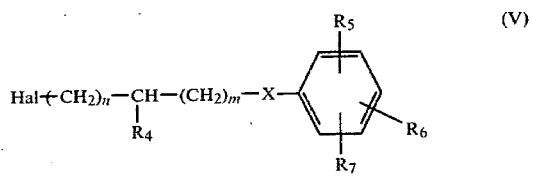

in which $R_4$, $R_5$, $R_6$, $R_7$, X, m and n have the meanings given for formula (I), and Hal is halogen, advantageously chlorine or bromine, with piperazine.

Said reaction may be effected within a solvent such as dimethylketone, ethylmethylketone, water, ethanol. The reaction is preferably effected at the reflux temperature of the solvent, in the presence of an acid-binding agent such as an alkali metal carbonate.

When X is oxygen or sulfur, the compounds of the formula (V) are obtained by reacting a phenol or thiophenol having the formula:

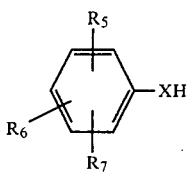  (VI)

in which $R_5$, $R_6$, $R_7$ and X have the above-defined meanings, with a dihalo derivative having the formula:

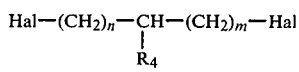  (VII)

in which $R_4$, m and n are as previously defined, within a solvent such as water, an alcohol, an aqueous-alcoholic mixture in the presence of an alkaline agent, generally sodium hydroxide.

Methods for the preparation of derivatives of the formula (V) in which X is a single bond are currently described in the literature.

As a modification, the compounds of the formula (I) may also be prepared:
by reaction of a benzamidine having the formula:

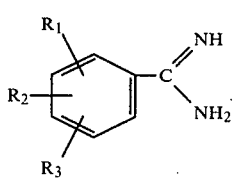

in which $R_1$, $R_2$ and $R_3$ have the meanings given for formula (I), with a piperazine of the formula (III) dissolved in a refluxing solvent such as methanol, ethanol or isopropanol;
by reaction of a S-methyl thiobenzimidate hydroiodide having the formula:

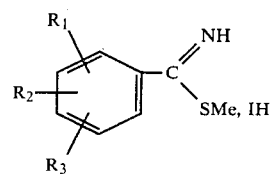

in which $R_1$, $R_2$ and $R_3$ have the meanings given for formula (I), with a piperazine of the formula (III) in an alcohol solvent. The S-methyl thiobenzimidates are obtained in conventional manner, by reaction, in acetone, of a benzothioamide with methyl iodide.

The compounds of the formula (I) may also be obtained by reaction of an organomagnesium compound having the formula:

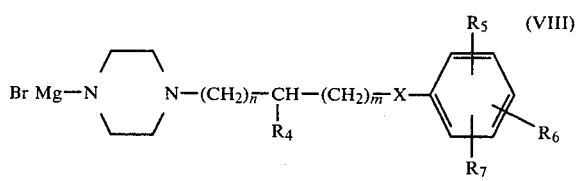  (VIII)

with a nitrile of the formula (IV) as previously defined, and hydrolysis of the reaction product according to the following scheme:

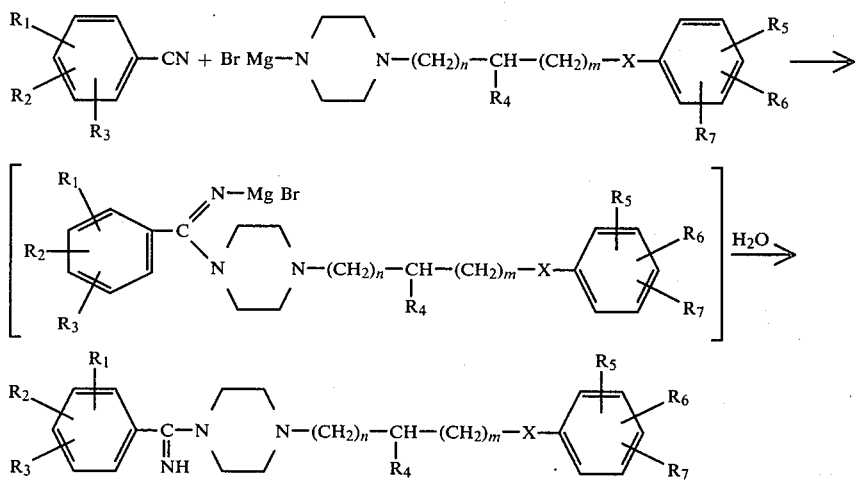

The compounds of the formula (VIII) are obtained in conventional manner from compounds of the formula (III).

The following non-limiting Examples illustrate the present invention.

Examples A–K illustrate the preparation of compounds of the formula (III). Examples 1–20 illustrate the preparation of compounds of the formula (I).

I-PREPARATION OF COMPOUNDS OF THE FORMULA (III)

EXAMPLE A 1-(2-Phenyl-propyl)piperazine

A solution of piperazine (344 g), β-bromoisopropylbenzene (199 g) in water (1 liter) and ethanol (0.35 liter) is refluxed for 24 hours. After cooling, the resulting amine is extracted with 3×0.5 liter methylene chloride.

After washing with water and evaporation of the solvent in vacuo, the resulting 2-phenylpropyl piperazine is distilled; b.p.=163°–165° C./15 mm Hg.

N.M.R. (CCl₄)  s(1H) 1.1 ppm   m (6H) 2.3 ppm
Ref: TMS       d (3H) 1.2 ppm   m (5H) 2.7 ppm
               s (5H) 7.2 ppm

EXAMPLE B

1-[2-(2,6-Dimethyl-phenoxy)-ethyl]piperazine (a) 2-(2,6-Dimethyl-phenoxy)-1-bromo-ethane To a solution containing sodium hydroxide (80 g) in water (1 liter) and ethanol (0.5 liter) are added 2,6-dimethyl-phenol (245 g) dissolved in ethanol (0.5 liter), and then dibromoethane (750 g). The mixture is refluxed for 48 hours, under vigorous stirring. It is then extracted with methylene chloride. After washing with dilute aqueous sodium hydroxide and then with water, the solvent is evaporated in vacuo. 2(2,6-Dimethyl-phenoxy)-1-bromo-ethane boils at 148°–150° C./25 mm Hg.

(b) 1-[2-(2,6-Dimethyl-phenoxy)ethyl]piperazine

To methylethylketone (1 liter) are added 2-(2,6-dimethylphenoxy)-1-bromo-ethane (132 g), sodium iodide (85 g), potassium carbonate (80 g) and piperazine (200 g). The mixture is refluxed for 24 hours, with stirring. After cooling, the mixture is filtered and then washed with 3×300 ml benzene. After evaporation of the benzene, the piperazine derivative is distilled; b.p. 25 mm Hg=190° C.

Using the procedure described in Examples A and B, the following compounds were prepared:

EXAMPLE C

1-[3-(2,6-Dimethyl-phenoxy)propyl]piperazine, b.p./13 mm Hg=195° C.

EXAMPLE D 1-(2-Phenoxy-ethyl)piperazine, b.p./13 mm Hg=190° C.

EXAMPLE E 1-(3-Phenoxy-propyl)piperazine; B.p./13 mm Hg=190° C.

EXAMPLE F

1-[2-(2-Methyl-phenoxy)-ethyl]piperazine; b.p./0.2 mm Hg=114°–116° C.

EXAMPLE G 1-(2-Phenyl-ethyl)piperazine; b.p./13 mm Hg=160°–165° C.

EXAMPLE H 1-(3-Phenyl-propyl)piperazine; b.p./25 mm Hg=185°–190° C.

EXAMPLE I 1-(2-Phenylthio-ethyl)-piperazine; b.p./0.05 mm Hg=140°–141° C.

EXAMPLE J 1-(2-Phenoxy-1-methyl-ethyl)piperazine; b.p./0.1 mm Hg=104°–105° C.

EXAMPLE K 1-(3-Phenoxy-2-hydroxy-propyl)-piperazine; b.p./13 mm Hg=205°–207° C.

II-PREPARATION OF COMPOUNDS OF THE FORMULA (I)

EXAMPLE 1

1-[2-(2,6-Dimethyl-phenoxy)ethyl]-4-(3-trifluoromethylbenzimidoyl)-piperazine dihydrochloride Ethyl 3-trifluoromethyl-phenyl-iminoate hydrochloride (5.4 g) and 1-[2-(2,6-dimethyl-phenoxy)ethyl]piperazine (5 g) in methanol (50 ml) are refluxed for 24 hours. After cooling, the reaction mixture is made acidic and the solvent is evaporated off. 1-[2-(2,6-Dimethyl-phenoxy)ethyl]-4-(3-trifluoromethyl-benzimidoyl)-piperazine dihydrochloride is recrystallized from absolute ethanol, as white crystals which melt at 202°–204° C.

NMR (DMSO d₆, Ref: TMS)
s (6H) 2.35 ppm,   m (10H) 3.8 ppm,
t (2H) 4.3  ppm,   s (3H) 7.15 ppm,   m (4H) 8.15 ppm
s (1H) 10.2 ppm,   s (1H) 10.4 ppm,   s (1H) 12.7 ppm

EXAMPLE 2

1-[2-(2,6-Dimethyl-phenoxy)ethyl]-4-(benzimidoyl)piperazine dihydrochloride

METHOD 1

To 1.2 g magnesium in ethyl ether (10 ml) is added ethyl bromide (7.5 ml). After dissolution of the magnesium, 1-[2-(2,6-dimethyl-phenoxy)ethyl]piperazine (0.03 mole) in ethyl ether (100 ml) is added thereto, after which the reaction mixture is refluxed for 30 minutes. After cooling, benzonitrile (10.3 g) in ether (100 ml) is added and the mixture is refluxed for 3 hours. An aqueous solution of ammonium chloride (100 ml) is added to the mixture. The ether phase is washed with water. After precipitation with ethereal hydrochloric acid, the resulting compound is recrystallized from methanol. M.p.=231°–232° C.

| N.M.R. (DMSO-d6) | s (6H) 2.35 ppm, t (2H) 4.35 ppm, s (5H) 7.8 ppm s (1H) 10.2; 10.4; 12.7 ppm | m (10H) 3.7 ppm s (3H) 7.15 ppm |
| --- | --- | --- |

METHOD 2

Benzamidine hydrochloride (0.1 mole) and 1-[2-(2,6-dimethylphenoxy)ethyl]piperazine (0.1 mole) in isopropanol (300 ml) are refluxed while nitrogen gas is bubbled through. Reflux is maintained for 72 hours. After cooling, the reaction medium is made acidic with a methanol solution of hydrochloric acid. After concentration of the solvent, the resulting precipitate is suction filtered and recrystallized from anhydrous ethanol, to give a product analogous to that obtained using Method 1.

METHOD 3

S-Methyl thiobenzimidate hydroiodide (0.1 mole) is dissolved in anhydrous ethanol (100 ml), and 1-[2-(2,6-dimethyl-phenoxy)-ethyl]piperazine (0.1 mole) is then added. The resulting material is refluxed for 12 hours. The alcohol is then evaporated off and a N sodium hydroxide solution (100 ml) is added to the residue which is then extracted with ether and washed with water. After acidification of the ether phase, the resulting precipitate is suction filtered and crystallized from anhydrous ethanol, to give a product analogous to that obtained using Methods 1 and 2.

Using the same procedure as in Example 1 or Example 2, the following compounds were prepared:

EXAMPLE 3

1-(2-Phenyl-ethyl)-4-(4-chloro-benzimidoyl)piperazine dihydrochloride M.p.=244°–245° C.

| N.M.R. (D2O) | s (4H) 7.7 ppm, s (5H) 7.3 ppm | m (112H) 3.5 ppm |
| --- | --- | --- |

EXAMPLE 4

1-(2-Phenoxy-ethyl)-4-(4-chloro-benzimidoyl)-piperazine dihydrochloride M.p.=217°–218° C.

| N.M.R. (DMSO d6, D2O) | s (4H) 7.85 ppm, m (5H) 7.3 ppm | m (12H) 3.8 ppm |
| --- | --- | --- |

EXAMPLE 5

1-(2-Phenoxy-ethyl)-4-(3-trifluoromethyl-benzimidoyl)-piperazine dihydrochloride M.p.=217°–218° C.

| N.M.R. (D2O) | m (4H) 8.15 ppm, t (5H) 4.55 ppm, m (10H) 3.90 ppm | m (5H) 7.4 ppm t (2H) 4.4 ppm |
| --- | --- | --- |

EXAMPLE 6

1-(2-Phenyl-propyl)-4-(benzimidoyl)piperazine dihydrochloride M.p.=216°–217° C.

| N.M.R. (D2O) | d (3H) 1.5 ppm, s (5H) 7.6 ppm, m (9H) 3.8 ppm | s (5H) 7.9 ppm t (2H) 4.25 ppm |
| --- | --- | --- |

EXAMPLE 7

1-(3-Phenoxy-propyl)-4-(2,6-dichloro-benzimidoyl)piperazine dihydrochloride M.p.=210°–211° C.

| N.M.R. (D2O) | m (2H) 2.4 ppm, s (3H) 7.9 ppm, m (5H) 7.4 ppm | m (4H) 4.4 ppm m (8H) 3.8 ppm |
| --- | --- | --- |

EXAMPLE 8

1-[2-(2,6-Dimethyl-phenoxy)-ethyl]-4-(2,6-dichloro-benzimidoyl)-piperazine dihydrochloride M.p.=250° C.

| N.M.R. (D2O) | s (6H) 2.35 ppm, m (10H) 3.85 ppm, s (3H) 7.3 ppm | t (2H) 4.3 ppm s (3H) 7.9 ppm |
| --- | --- | --- |

EXAMPLE 9

1-(2-Phenoxy-ethyl)-4-(2,6-dichloro-benzimidoyl)-piperazine dihydrochloride M.p.=250° C.

| N.M.R. (D2O) | s (3H) 7.8 ppm, m (5H) 7.4 ppm | m (12H) 3.7 ppm |
| --- | --- | --- |

EXAMPLE 10

1-[3-(2,6-Dimethyl-phenoxy)-propyl]-4-(2,6-dichloro-benzimidoyl)-piperazine dihydrochloride M.p.=245°–246° C.

| N.M.R. (DMSO d6) | s (6H) 2.35 ppm, s (1H) 11.6; 10.8; 11 ppm; r (14H) 3.7 ppm | s (3H) 7.15 ppm s (3H) 7.9 ppm |
| --- | --- | --- |

EXAMPLE 11

1-[2-(2-Methyl-phenoxy)ethyl]-4-(benzimidoyl)-piperazine dihydrochloride M.p.=240°–241° C.

| N.M.R. (D2O) | s (3H) 2.35 ppm, t (2H) 4.3 ppm, m (4H) 7.3 ppm | m (10H) 3.85 ppm s (5H) 7.9 ppm |
| --- | --- | --- |

EXAMPLE 12

1-[2-(2,6-Dimethyl-phenoxy)-ethyl]-4-(4-chloro-benzimidoyl)-piperazine dihydrochloride M.p.=214°–215° C.

| N.M.R. (DMSO d6) | s (6H) 2.35 ppm, t (2H) 4.3 ppm, | m (10H) 3.85 ppm s (3H) 7.3 ppm |
| --- | --- | --- |

-continued

| | | |
|---|---|---|
| | s (4H) 7.9 ppm; | s (1H) 19; 10.3; 12.5 ppm |

EXAMPLE 13

1-[3-(2,6-Dimethyl-phenoxy)-propyl]-4-(3-trifluoromethyl-benzimidoyl)-piperazine dihydrochloride M.p.=250° C.

| N.M.R. (D$_2$O) | s (6H) 2.35 ppm, | m (14H) 3.8 ppm |
|---|---|---|
| | s (3H) 7.3 ppm, | m (4H) 8.2 ppm |

EXAMPLE 14

1-(3-Phenyl-propyl)-4-(3-trifluoromethyl-benzimidoyl)-piperazine dihydrochloride M.p.=223°–225° C.

| N.M.R. (D$_2$O) | s (5H) 7.6 ppm, | m (2H) 2.5 ppm |
|---|---|---|
| | s (4H) 8.2 ppm, | m (12H) 3.8 ppm |

EXAMPLE 15

1-(3-Phenyl-propyl)-4-(benzimidoyl)-piperazine hydrochloride M.p.=245°–247° C.

| N.M.R. (MeOH d$_4$) | s (5H) 7.75 ppm, | m (2H) 2.2 ppm |
|---|---|---|
| | t (2H) 4.25 ppm, | s (5H) 7.3 ppm |
| | t (2H) 2.7 ppm, | m (8H) 3.5 ppm |

EXAMPLE 16

1-[3-(2,6-Dimethyl-phenoxy)-propyl]-4-benzimidoyl piperazine dihydrochloride M.p.=228°–230° C.

| N.M.R. (DMSO d$_6$) | s (6H) 2.35 ppm, | s (5H) 7.9 ppm |
|---|---|---|
| | s (3H) 7.3 ppm, | m (14H) 4.0 ppm |
| | s (1H) 10.0; 10.3; 12.5 ppm | |

EXAMPLE 17

1-(3-Phenoxy-propyl)-4-(4-chloro-benzimidoyl)-piperazine dihydrochloride M.p.=245°–246° C.

| N.M.R. (DMSO d$_6$) | s (1H) 12.0 ppm, | s (4H) 7.5 ppm |
|---|---|---|
| | s (1H) 10.1 ppm, | m (5H) 6.8 ppm |
| | s (1H) 9.8 ppm | |

EXAMPLE 18

1-(2-Phenoxy-ethyl)-4-(benzimidoyl)-piperazine dihydrochloride M.p.=250° C.

| N.M.R. (DMSO d$_6$) | s (5H) 7.7 ppm, | m (5H) 7.1 ppm |
|---|---|---|
| | t (2H) 4.0 ppm, | m (10H) 3.5 ppm |
| | s (1H) 9.8 ppm, | s (1H) 10.3 ppm |
| | s (1H) 11.5 ppm | |

EXAMPLE 19

1-(3-Phenylthio-propyl)-4-(benzimidoyl)-piperazine dihydrochloride M.p.=245° C.

| N.M.R. (D$_2$O) | s (5H) 7.8 ppm, | t (2H) 4.5 ppm |
|---|---|---|
| | m (10H) 3.9 ppm, | s (5H) 8.1 ppm |
| | t (2H) 3.4 ppm, | m (2H) 2.4 ppm; |

EXAMPLE 20

1-(3-Phenoxy-propyl)-4-(benzimidoyl)-piperazine dihydrochloride M.p.=255° C.

| N.M.R. (DMSO d$_6$) | s (5H) 7.7 ppm, | t (2H) 4.0 ppm |
|---|---|---|
| | m (10H) 3.5 ppm, | m (5H) 7.1 ppm |
| | m (2H) 2.2 ppm, | s (1H) 9.9 ppm; |
| | | 10.3 ppm; 11.5 ppm |

EXAMPLE 21

1-[2-(2,6-Dimethyl-phenoxy)-ethyl]-4-(2-chloro-benzimidoyl)-piperazine dihydrochloride M.p.=270° C.

| N.M.R. (D$_2$O) | s (6H) 2.4 ppm, | m (12H) 4.2 ppm |
|---|---|---|
| | s (4H) 7.9 ppm, | s (3H) 7.3 ppm |

EXAMPLE 22

1-[2-(2,6-Dimethyl-phenoxy)-ethyl]-4-(3-chloro-benzimidoyl)-piperazine dihydrochloride M.p.=170° C.

| N.M.R. (D$_2$O) | s (6H) 2.6 ppm, | m (4H) 8.1 ppm |
|---|---|---|
| | s (3H) 7.5 ppm | |

EXAMPLE 23

1-[2-(2,6-Dimethyl-phenoxy)-ethyl]-4-(2-chloro-6-methoxy-benzimidoyl)-piperazine dihydrochloride M.p.=265° C.

| N.M.R. (D$_2$O) | s (3H) 7.3 ppm, | m (12H) centered at 4 ppm |
|---|---|---|
| | s (6H) 2.6 ppm | s (3H) 4.2 ppm |
| | m (3H) 7.7 ppm | |

EXAMPLE 24

1-[2-(2,6-Dimethyl-phenoxy)-ethyl]-4-(2-chloro-6-methyl-benzimidoyl)-piperazine dihydrochloride M.p.=250° C.

| N.M.R. (D$_2$O) | s (6H) 2.4 ppm, | m (12H) 4.2 ppm |
|---|---|---|
| | s (3H) 2.5 ppm, | s (3H) 7.2 ppm |
| | s (3H) 7.8 ppm | |

EXAMPLE 25

1-[2-(2,6-Dimethyl-phenoxy)-ethyl]-4-(4-methyl-benzimidoyl)-piperazine dihydrochloride M.p.=270° C.

| N.M.R. (D$_2$O) | s (4H) 7.7 ppm, | s (6H) 2.4 ppm |
|---|---|---|
| | s (3H) 7.15 ppm, | s (3H) 2.6 ppm |

-continued m (12H) 4.3 ppm

EXAMPLE 26

1-[2-(2,6-Dimethyl-phenoxy)-ethyl]-4-(3-methyl-benzimidoyl)-piperazine dihydrochloride M.p.=260° C.

| N.M.R. (D₂O) | s (4H) 7.7 ppm | s (6H) 2.4 ppm |
|---|---|---|
| | s (3H) 7.1 ppm | s (3H) 2.5 ppm |

EXAMPLE 27

1-[2-(2,6-Dimethyl-phenoxy)-ethyl]-4-(2-methyl-benzimidoyl)-piperazine dihydrochloride M.p.=264° C.

| N.M.R. (D₂O) | s (4H) 7.7 ppm | s (3H) 7.3 ppm |
|---|---|---|
| | s (6H) 2.4 ppm | s (3H) 2.6 ppm |

EXAMPLE 28

1-[2-(2,6-Dimethyl-phenoxy)-ethyl]-4-(4-benzyloxy-benzimidoyl)-piperazine dihydrochloride M.p.=260° C.

EXAMPLE 29

1-(2-Phenyl-propyl)-4-(4-benzyloxy-benzimidoyl)-piperazine dihydrochloride M.p.=280° C.

EXAMPLE 30

1-[2-(2-Chloro-5-methoxy)-ethyl]-4-benzimidoyl-piperazine dihydrochloride M.p.=263° C.

EXAMPLE 31

1-[2-(3,5-Dimethyl-4-chloro-phenoxy)-ethyl]-4-benzimidoyl-piperazine dihydrochloride M.p.=250° C.

EXAMPLE 32

1-[3,5-Dimethyl-4-chloro-phenoxy)-propyl]-4-benzimidoyl-piperazine dihydrochloride M.p.=265° C.

EXAMPLE 33

1-[2-(2,6-Dimethyl-phenoxy)-ethyl]-4-(4-hydroxy-benzimidoyl)-piperazine dihydrochloride M.p.=235° C.

EXAMPLE 34

1-(2-Phenyl-propyl)-4-(4-hydroxy-benzimidoyl)piperazine dihydrochloride M.p.=210° C.

EXAMPLE 35

1-(2-Phenyl-propyl)-4-(2-benzyloxy-benzimidoyl)-piperazine dihydrochloride M.p.=254° C.

EXAMPLE 36

1-[2-(2,6-Dimethyl-phenoxy)-ethyl]-4-(3-benzyloxy-benzimidoyl)-piperazine dihydrochloride M.p.=245° C.

EXAMPLE 37

1-[2-(2,6-Dimethyl-phenoxy)-ethyl]-4-(2-benzyloxy-benzimidoyl)-piperazine dihydrochloride M.p.=210° C.

EXAMPLE 38

1-(2-Phenyl-propyl)-4-(3-benzyloxy-benzimidoyl)-piperazine dihydrochloride M.p.=240° C.

EXAMPLE 39

1-(2-Phenyl-propyl)-3-(3-hydroxy-benzimidoyl)-piperazine dihydrochloride M.p.=270° C.

EXAMPLE 40

1-[2-(2,6-Dimethyl-phenoxy)-ethyl]-4-(2-hydroxy-benzimidoyl)-piperazine dihydrochloride M.p.=200° C.

EXAMPLE 41

1-[2-(2,6-Dimethyl-phenoxy)-ethyl]-4-(3-hydroxy-benzimidoyl)-piperazine dihydrochloride M.p.=200° C.

The compounds of the formula (I) and their pharmaceutically acceptable acid addition salts have useful activities at the cardiovascular level and, more particularly, antiarrhythmic properties, and are therapeutically useful for the control of the cardiovascular system.

Corrector Activity of the Anomalies of the Cardiac Rhythm

This activity was evidenced in pentobarbital-anesthetized dogs exhibiting arrhythmia and ventricular tachycardia following injection of a specific dosage (40–100 γ/kg) of ouabaine.

The compounds of the formula (I), and more particularly the compounds of Examples 2,6,28,29,33,36,38,39,40 and 41, on intravenous administration at single dosages of 0,5–5 mg/kg, induce protection against ouabaine-induced arrhythmia.

The oral toxicity (LD 50) of the compounds of the formula (I) in rats is between 400 and 1,100 mg/kg.

On the other hand, the compounds of the formula (I) are free from any harmful side-effects.

Thus, this invention includes also within its scope therapeutic compositions comprising a compounds of the formula (I) or a pharmaceutically acceptable acid addition salt thereof, typically together with a pharmaceutically acceptable excipient.

The therapeutic compositions of this invention may be administered to humans by the oral or parenteral routes.

Said compositions may typically be formulated as capsules, tablets, or injectable ampoules.

Depending on the route of adminstration, the compositions may typically contain 1–60 wt% active ingredient together with a pharmaceutically acceptable excipient.

The daily dosage regimen for adult patients may be from 50 mg to 1,000 mg active ingredient by the oral route and from 30 mg to 600 mg active ingredient by the parenteral route.

Examples of therapeutic compositions of this invention are given below.

(a) Injectable ampoule

| | |
|---|---|
| Compound of Example 2 | 30 mg |
| Buffered excipient, sufficient to make | 5 ml |

(b) Capsules

| | |
|---|---|
| Compound of Example 2 | 40 mg |
| Lactose | 153 mg |
| Talc | 5 mg |
| Magnesium stearate | 2 mg |

Having now described our invention what we claim as new and desire to secure by Letters Patent is:

1. A process for the treatment of cardiac rhythm disorders which comprises administering to a human in need thereof a therapeutic composition containing an anti-arrhythmic effective amount of 1-[2-(2,6-dimethyl-phenoxy)-ethyl]-4-(benzimidoyl)-piperazine or a pharmaceutically acceptabel acid addition salt thereof.

2. A therapeutic composition having anti-arrhythmic properties containing an anti-arrhythmic effective amount of 1-[2-(2,6-dimethyl-phenoxy)-ethyl]-4-(benzimidoyl)-piperazine or a pharmaceutically acceptable acid addition salt thereof.

3. 1-[2-(2,6-Dimethyl-phenoxy)-ethyl]-4-(benzimidoyl)-piperazine and its pharmaceutically acceptable acid addition salts.

* * * * *